US00PP30136P2

(12) United States Plant Patent
Ammerlaan

(10) Patent No.: US PP30,136 P2
(45) Date of Patent: Jan. 22, 2019

(54) ***GASTERALOE* PLANT NAMED 'OVROCKS02'**

(50) Latin Name: ***Gasteraloe* Guillaumin**
Varietal Denomination: OVROCKS02

(71) Applicant: Johannes Hendrikus Adrianus Ammerlaan, Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/731,952

(22) Filed: Aug. 31, 2017

(30) Foreign Application Priority Data

Jul. 18, 2017 (QZ) ..... PBR 2017/1825

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Anne Marie Grunberg
(74) *Attorney, Agent, or Firm* — Samuel R. McCoy, Jr.

(57) ABSTRACT

A new and distinct cultivar of *Gasteraloe* plant named 'OVROCKS02' which is characterized by a globular profile with upright foliage spirally arranged in a short, compact rosette, dark green foliage with light green leaf margins, and foliage which is densely covered with prominent light green papillae, as well as the stability of these characteristics from generation to generation.

4 Drawing Sheets

Latin name of the genus and species: The Latin name of the genus and species of the novel variety disclosed herein is *Gasteraloe* Guillaumin.

Variety denomination: The inventive variety of *Gasteraloe* disclosed herein has been given the variety denomination 'OVROCKS02'.

CROSS REFERENCE TO RELATED APPLICATIONS

This application claims priority to the Community Plant Variety Rights application number 2017/1825, filed on Jul. 18, 2017, which is herein incorporated by reference.

BACKGROUND OF THE INVENTION

Parentage: 'OVROCKS02' originated as a naturally occurring, whole-plant mutation of an unnamed *Gasteraloe* plant (not patented). In November of 2012 the inventor discovered the mutation at a commercial greenhouse in Bleiswijk, the Netherlands, growing amongst a crop of the parent plant. The mutation was noted for its unique foliage and growth habit and was subsequently isolated for further evaluation in order to confirm the distinctness and stability of the characteristics first observed. Upon confirmation of distinctness and stability, 'OVROCKS02' was selected for commercialization.

Asexual Reproduction: Asexual reproduction of the new cultivar 'OVROCKS02', by way of rooting leaf cuttings, was first initiated in November of 2012 at the inventor's commercial greenhouse in Bleiswijk, the Netherlands. The claimed plant has since been asexually propagated by way of meristematic tissue culture propagation. Through five subsequent generations, the unique features of this cultivar have proven to be stable and true to type.

SUMMARY OF THE INVENTION

The cultivar 'OVROCKS02' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS02'. These characteristics in combination distinguish 'OVROCKS02' as a new and distinct *Gasteraloe* cultivar:

1. 'OVROCKS02' exhibits a globular profile with upright foliage which is spirally arranged in a short, compact rosette; and
2. 'OVROCKS02' exhibits narrowly deltoid foliage with a narrowly apiculate apex and a soft mucronate tip; and
3. 'OVROCKS02' exhibits foliage that is dark green with light green leaf margins, and densely covered with prominent light green papillae; and
4. 'OVROCKS02' exhibits papillae on the abaxial leaf surface which are arranged in distinct axial rows.

BOTANICAL DESCRIPTION OF THE PLANT

Figure 1:
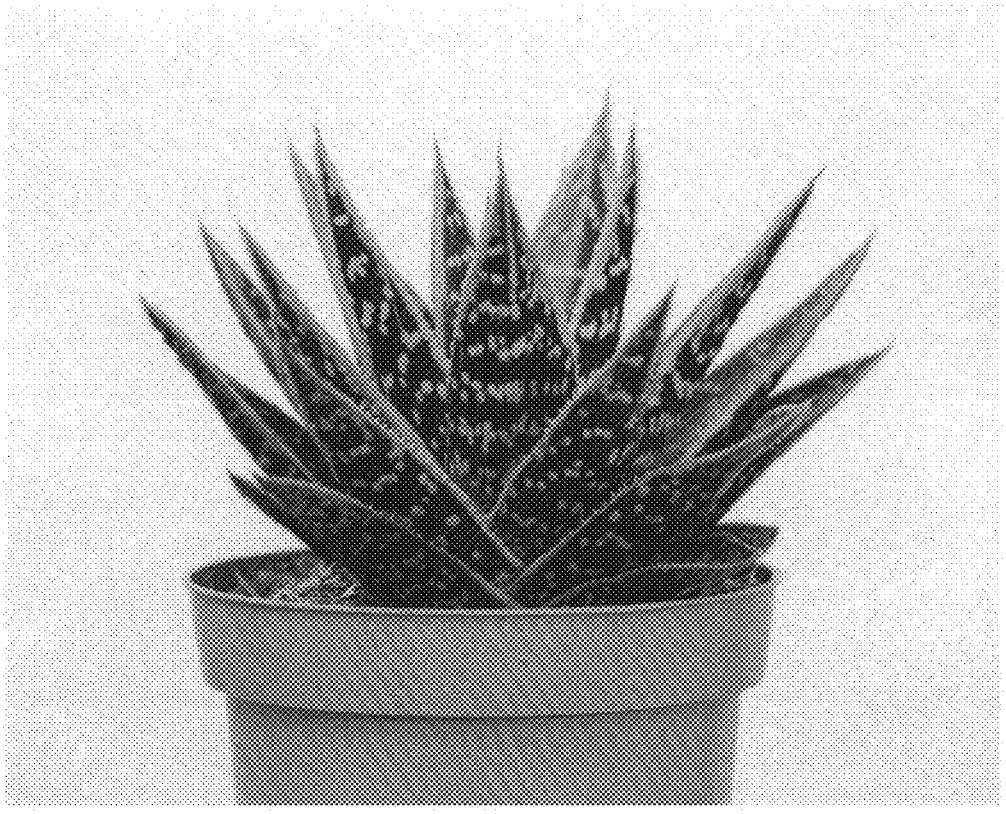
FIG. 1 illustrates, as nearly true as it is reasonably possible to make the same in color photographs of this type, an exemplary plant of 'OVROCKS02' grown in a commercial greenhouse in Bleiswijk, the Netherlands. This plant is approximately 16 months old, shown planted in a 10.5 cm container.
Figure 2:
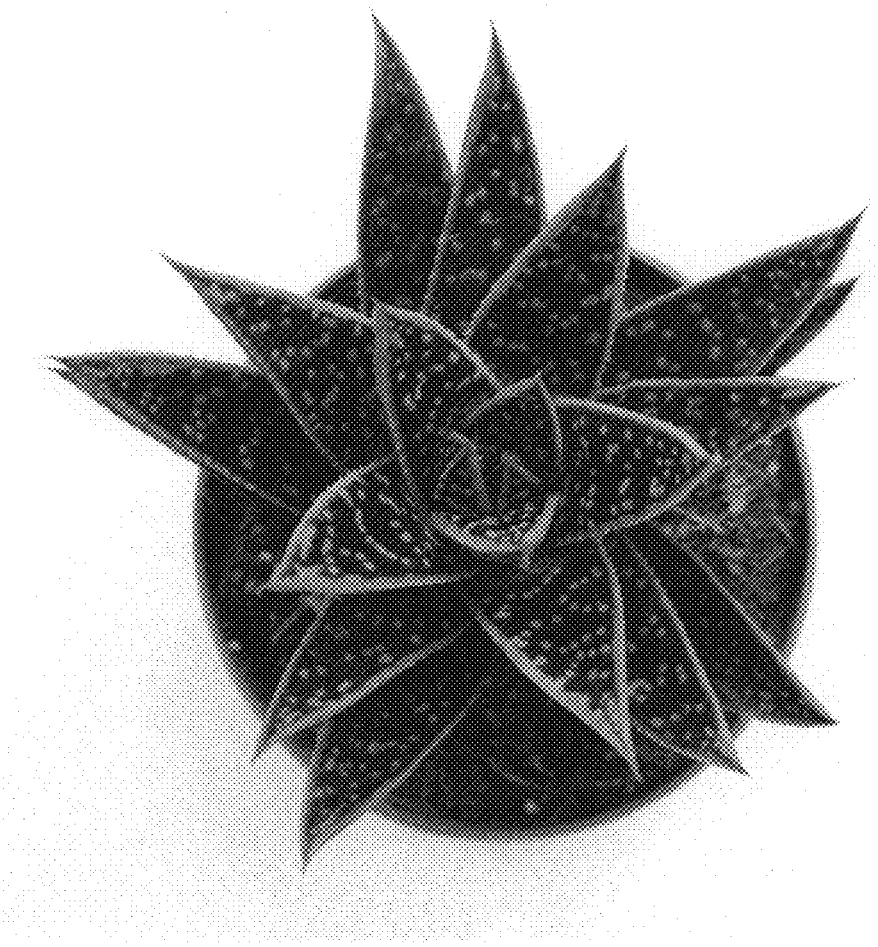
FIG. 2 illustrates, as nearly true as it is reasonably possible to make the same in color photographs of this type, the typical foliage arrangement of 'OVROCKS02'.
Figure 3:
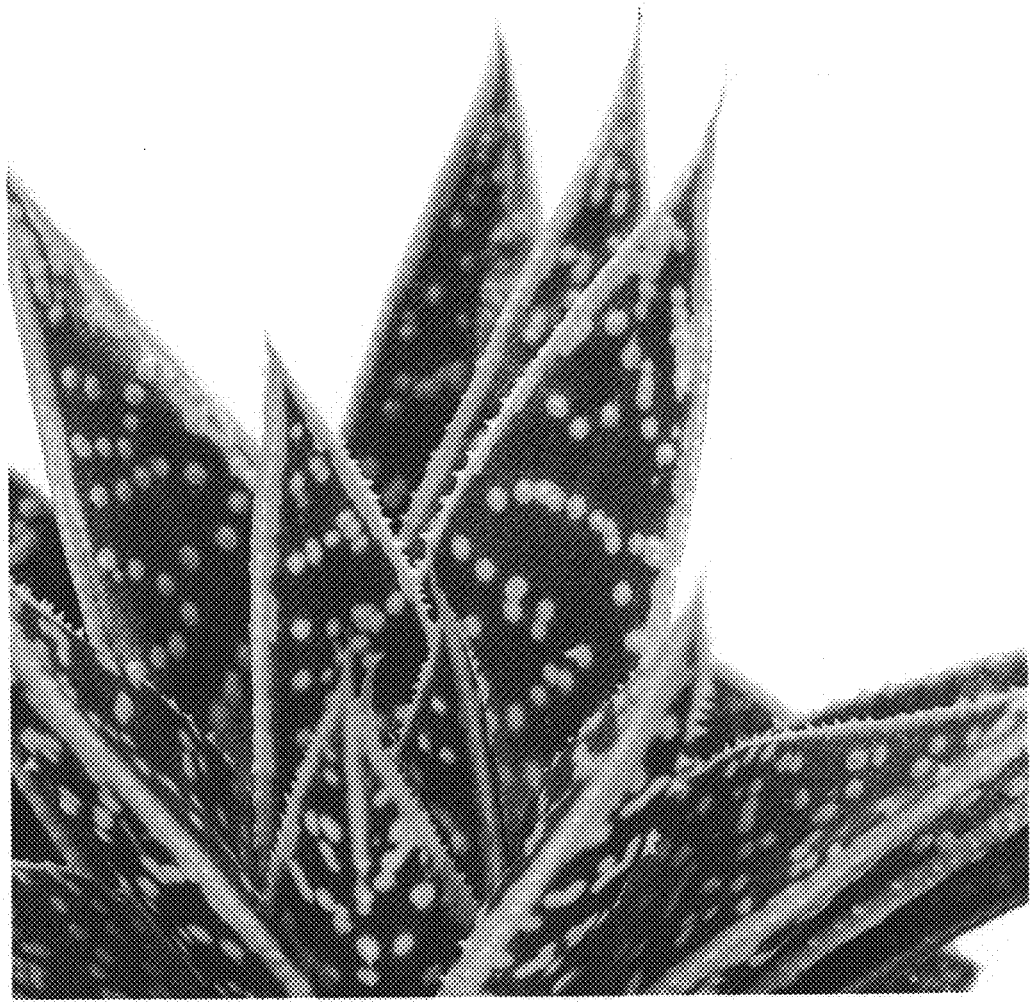
FIG. 3 illustrates, as nearly true as it is reasonably possible to make the same in color photographs of this type, the adaxial surface of the mature foliage 'OVROCKS02'.
Figure 4:
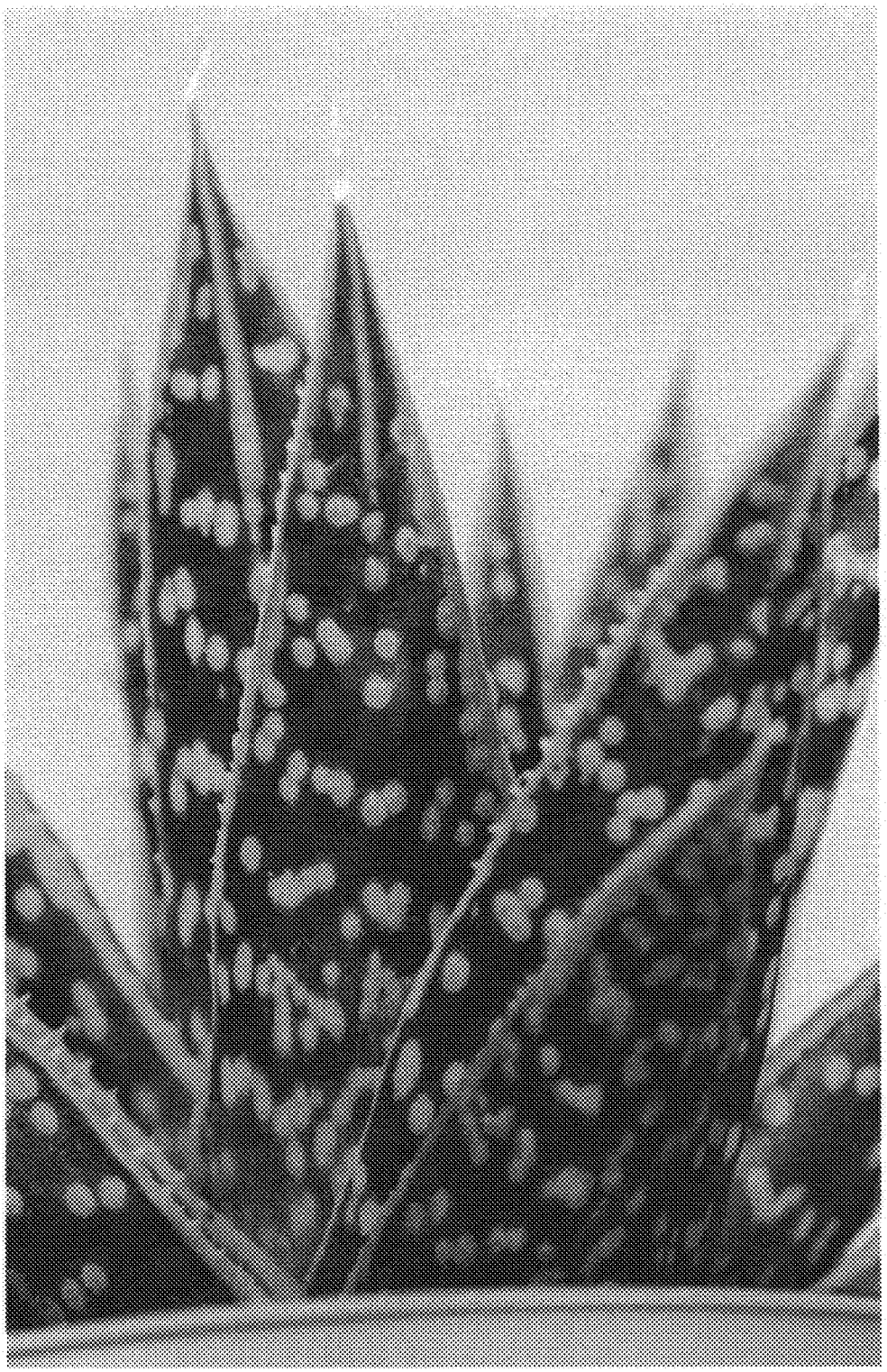
FIG. 4 illustrates, as nearly true as it is reasonably possible to make the same in color photographs of this type, the abaxial surface of the mature foliage 'OVROCKS02'.

The following observations and measurements made in June of 2017 describe averages from a sample set of six specimens of 16 months old 'OVROCKS02' plants grown in 10.5 cm nursery containers at commercial greenhouse in Bleiswijk, the Netherlands. Plants were produced using conventional greenhouse production protocols for *Gasteraloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS02' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS02' and a comparison with the parent and closest known comparator is provided below.

Plant description:

*Growth habit*.—Succulent perennial with foliage growing in a non-branched basal rosette.

*Plant form*.—Globular; compact.

*Height from soil level to top of foliar plane*.—11.1 cm.

*Plant spread*.—Average of 15.4 cm.

*Growth rate*.—Moderate.

*Plant vigor*.—Moderate.

*Propagation*.—Type — Leaf cuttings. Time to initiate rooting — Approximately 90 days at 21 degrees Celsius. Crop time — Approximately 16 months to produce a marketable plant in a 10.5 cm container.

*Disease and pest resistance or susceptibility*.—Neither resistance nor susceptibility to typical *Gasteraloe* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Spirally placed in a rosette.

*Division*.—Simple.

*Attachment*.—Sessile.

*Quantity*.—Approximately 25 leaves per rosette.

*Shape*.—Narrow deltoid succulent leaves.

*Dimensions*.—9.2 cm long, 3.1 cm wide, and 0.9 cm thick, on average.

*Aspect*.—Slightly concave to flat.

*Attitude*.—Distal portion of the leaf is lightly curved upward in an average angle of 10 degrees to the remainder of the leaf blade.

*Apex*.—Narrow apiculate with a soft mucronate tip.

*Base*.—Broad cuneate.

*Margin*.—Dentate; teeth have an average length of 0.1 cm and are colored yellow-green, nearest to RHS 147D but lighter. Margins are not undulated or lobed.

*Texture, adaxial surface*.—Glabrous and moderately covered with papillae, presenting as orbicular dots, each approximately 0.5 mm high and 0.5 mm in diameter; papilla bearing short, soft spines towards the apex; average length of the spines is 2.0 mm, at maturity.

*Texture, abaxial surface*.—Glabrous and densely covered with papillae, presenting as orbicular dots which are loosely arranged in axial rows across the leaf surface, each approximately 0.5 mm high and 0.5 mm in diameter; papilla bearing short, soft spines towards the apex; average length of the spines is 2.5 mm, at maturity.

*Luster, adaxial surface*.—Slightly to moderately glossy.

*Luster, abaxial surface*.—Slightly glossy.

*Color*.—Juvenile foliage, adaxial surface — Green, nearest to RHS 139A, and fading to yellow-green towards the base, nearest to RHS 144B; margined green-white, nearest to RHS 157C; leaf moderately covered with papillae which are colored green-white, nearest to a combination of RHS 157C and 157D. Juvenile foliage, abaxial surface — Nearest to a combination of green, RHS 139A, and yellow-green, nearest to a combination of RHS 147D; fading to yellow-green towards the base, nearest to a combination of RHS 144A and 144B; margined green-white, nearest to RHS 157C; leaf densely covered with papillae which are loosely arranged in axial rows across the leaf surface and colored green-white, nearest to RHS 157D. Mature foliage, adaxial surface — Nearest to in between green, RHS NN137A, and yellow-green, RHS 147A, but much darker; fading to yellow-green towards the base, nearest to RHS 148C; margined greyed-green, nearest to RHS 191A; leaf moderately covered with papillae which are colored greyed-green, nearest to RHS 191A. Mature foliage, abaxial surface — Nearest to in between green, RHS NN137A, and yellow-green, RHS 147A, but darker; fading to yellow-green towards the base, nearest to a combination of RHS 147B, 147C and 147D; margined greyed-green, nearest to RHS 191B; leaf densely covered with papillae which are loosely arranged in axial rows across the leaf surface and colored greyed-green, nearest to RHS 191B. Venation — No venation is visible.

*Petiole*.—No petiole; leaves are sessile.

Inflorescence: No flowering has been observed to date.

COMPARISONS WITH THE PARENT PLANT

Plants of the new cultivar 'OVROCKS02' differ from the parent, an unnamed *Gasteraloe* plant, in the following characteristics described in Table 1 below.

TABLE 1

| Characteristic | 'OVROCKS02' | The parent. |
|---|---|---|
| Foliage attitude. | Foliage is more upright. | Foliage has a more relaxed attitude. |
| Foliage apex. | Leaves are more point. | Leaves are less pointed. |
| General coloration of leaf margins. | Leaves are margined light green. | Leaves are not margined light green. |
| Foliage; occurrence of papillae. | Fewer papilla. | More papilla. |
| Foliage; prominence of spines on the papillae. | Papillae are larger. | Papillae are smaller. |

COMPARISONS WITH THE CLOSEST KNOWN COMPARATOR

Plants of the new cultivar 'OVROCKS02' differ from the commercial variety, *Gasteraloe* 'Tiki Tahi' (U.S. Pat. No. 23,913) in the following characteristics described in Table 2 below.

TABLE 2

| Characteristic | 'OVROCKS02' | 'Tiki Tahi' |
|---|---|---|
| Foliage aspect. | Slightly concave to flat. | Leaves are concave. |
| Length of foliage. | Shorter than 'Tiki Tahi'. | Longer than 'OVROCKS02'. |
| Thickness of foliage. | Thinner than 'Tiki Tahi'. | Thicker than 'OVROCKS02'. |
| General coloration of leaf margins. | Leaves are margined light green. | Leaves are margined white. |

That which is claimed is:

1. A new and distinct variety of *Gasteraloe* plant named 'OVROCKS02', substantially as described and illustrated herein.

* * * * *